United States Patent [19]
Tsukada et al.

[11] Patent Number: 6,090,087
[45] Date of Patent: Jul. 18, 2000

[54] SIMPLIFIED, AUTOMATIC OPENING AND CLOSING TYPE URINATION DEVICE

[75] Inventors: Osamu Tsukada, Nagano-ken; Yasuhiko Nakajima, Kanagawa-ken, both of Japan

[73] Assignee: Tsukada Medical Research Co., Ltd., Tokyo, Japan

[21] Appl. No.: 09/254,278

[22] PCT Filed: Jul. 4, 1997

[86] PCT No.: PCT/JP97/02325

§ 371 Date: Mar. 3, 1999

§ 102(e) Date: Mar. 3, 1999

[87] PCT Pub. No.: WO99/01092

PCT Pub. Date: Jan. 14, 1999

[51] Int. Cl.[7] .......................................... A61M 1/00
[52] U.S. Cl. ........................ 604/327; 604/544; 600/573; 600/579; 600/581
[58] Field of Search .................................... 604/327–331, 604/349, 544, 540, 317, 318; 600/573, 574, 579, 581

[56] References Cited

FOREIGN PATENT DOCUMENTS

| | | | |
|---|---|---|---|
| 4111961A1 | 10/1992 | Germany | ................................ 604/544 |
| 60-234668 | 11/1985 | Japan . | |
| 2-180271 | 7/1990 | Japan . | |
| 6-3348 | 1/1994 | Japan . | |

*Primary Examiner*—Mark O. Polutta
*Assistant Examiner*—Kelly M Cheney
*Attorney, Agent, or Firm*—Sughrue, Mion, Zinn, Macpeak & Seas, PLLC

[57] ABSTRACT

A simple automatic opening and closing type of urination apparatus (10) comprises a flexible tube (110), a plunger (120), a bearing table (130), an elastic member (140), an electromagnetic solenoid (150), and an actuator (160). The flexible tube (110) has an inlet port (111) and an outlet port (112). The plunger (120) has a pushing portion (121) at one end and a contact portion (122) at the other end. The bearing table (130) is disposed below the pushing portion (121) of the plunger (120) for supporting the flexible tube (110). The elastic member (140) normally biases the pushing portion (121) of the plunger (120) onto the flexible tube (110) on the bearing table (130) to squeeze the flexible tube (110) between the pushing portion (121) and the bearing table (130). The electromagnetic solenoid (150) selectively attracts and repulses the contact portion (122) of the plunger (120). The actuator (160) selectively couples the electromagnetic solenoid (150) to a power source (170). The inlet port (111) of the flexible tube (110) is connected through a catheter (11) to a urinary bladder (12) and the outlet port (112) of the flexible tube (110) is connected through a conduit tube (13) to a urine-collecting bag (14). The electromagnetic solenoid (150) is energized when a urine pressure in the urinary bladder (12) reaches a given value, thereby retracting the pushing portion (121) of the plunger (120) to release the flexible tube (110) from being squeezed.

7 Claims, 4 Drawing Sheets

SIMPLIFIED, AUTOMATIC OPENING AND CLOSING TYPE URINATION DEVICE

TECHNICAL FIELD

This invention relates to a simple automatic opening and closing type of urination apparatus which can be easily connected between a catheter and a urine-collecting bag and which facilitates automatic urine-storage and urination from a urinary bladder of a patient who carries out urination by insertion of the catheter into the urinary bladder.

BACKGROUND ART

It is necessary for a patient, who suffers from urinary disfunction to discharge urine out of the body through a urethra catheter left in the urinary bladder. To this end, several kinds of urination apparatus have been utilized. Most conventional urination apparatuses introduce urine into the urine-collecting bag through the urethra catheter inserted through the ureter into the urinary bladder and an on-off valve connected to an end of the urethra catheter. In such a urination apparatus, since urine always flows out of the body through the catheter left in the urinary bladder, the bladder does not expand and contract to effect normal urine-storage and urination and remains in an atrophied state. Consequently, the urinary bladder may completely lose its function after a long period of time.

Thus, several automatic urination apparatuses which actuate an on-off valve in response to detection of urine pressure in the urinary bladder have been proposed to maintain the function of the urinary bladder. However, these apparatuses have several problems in that they are large in scale, expensive, and inconvenient for a patient.

DISCLOSURE OF THE INVENTION

An object of the present invention is to provide a simple automatic opening and closing type of urination apparatus which enables a patient to collect urine while maintaining a normal function of a urinary bladder and which is inexpensive and simple in construction.

A simple automatic opening and closing type of urination apparatus in accordance with the present invention comprises mainly a flexible tube, a plunger, a bearing table, an elastic member, an electromagnetic solenoid, and an actuator. The flexible tube has an inlet port and an outlet port. The plunger has a pushing portion at one end and a contact portion at the other end. The bearing table is disposed below the pushing portion of the plunger to support the flexible tube. The elastic member normally biases the pushing portion of the plunger onto the flexible tube on the bearing table to squeeze the flexible tube between the pushing portion and the bearing table. The electromagnetic solenoid selectively attracts and repulses the contact portion of the plunger. The actuator selectively couples the electromagnetic solenoid to a power source.

In the above construction, the inlet port of the flexible tube is connected through a catheter to a urinary bladder and the outlet port of the flexible tube is connected through a conduit tube to a urine-collecting bag. The electromagnetic solenoid is energized when urine pressure in the urinary bladder reaches a given value, thereby retracting the pushing portion of the plunger to release the flexible tube from being squeezed.

The actuator may be any one of a balloon type pressure sensor, a timer, and a push button.

The power source may be any one of an AC source, a dry battery, and a storage battery.

The urine in a urinary bladder is discharged from one of the outlet ports in the flexible tube into a urine-collecting bag outside a patient's body when urine pressure in the urinary bladder reaches a predetermined value. Each of the outlet ports is set to correspond to each of the predetermined values of the pressure of urine in the urinary bladder communicated with the inlet port of the flexible tube. After completing urination the above operation is repeated. Thus, the urinary bladder can repeat its own expansion and contraction for urine-storage and urination as usual, although the urinary bladder is communicated with the urine-collecting bag through the catheter.

BEST MODE FOR CARRYING OUT THE INVENTION

Figure 1:
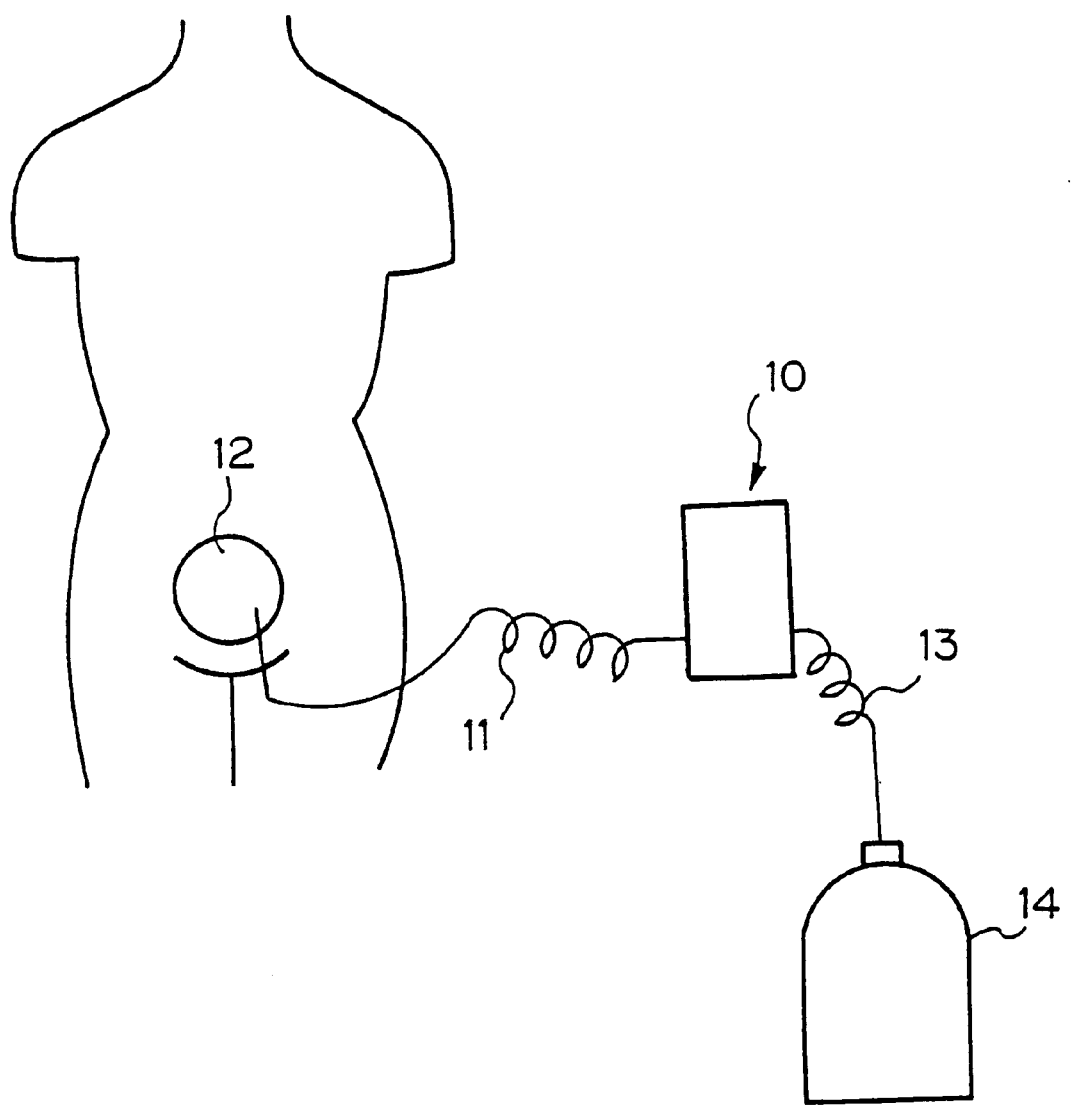
FIG. 1 is a schematic explanatory view of an example of use of a simple automatic opening and closing type of urination apparatus in accordance with the present invention.

Embodiments of a simple automatic opening and closing type of urination apparatus in accordance with the present invention will be explained below by referring now to the drawings.

Figure 2:
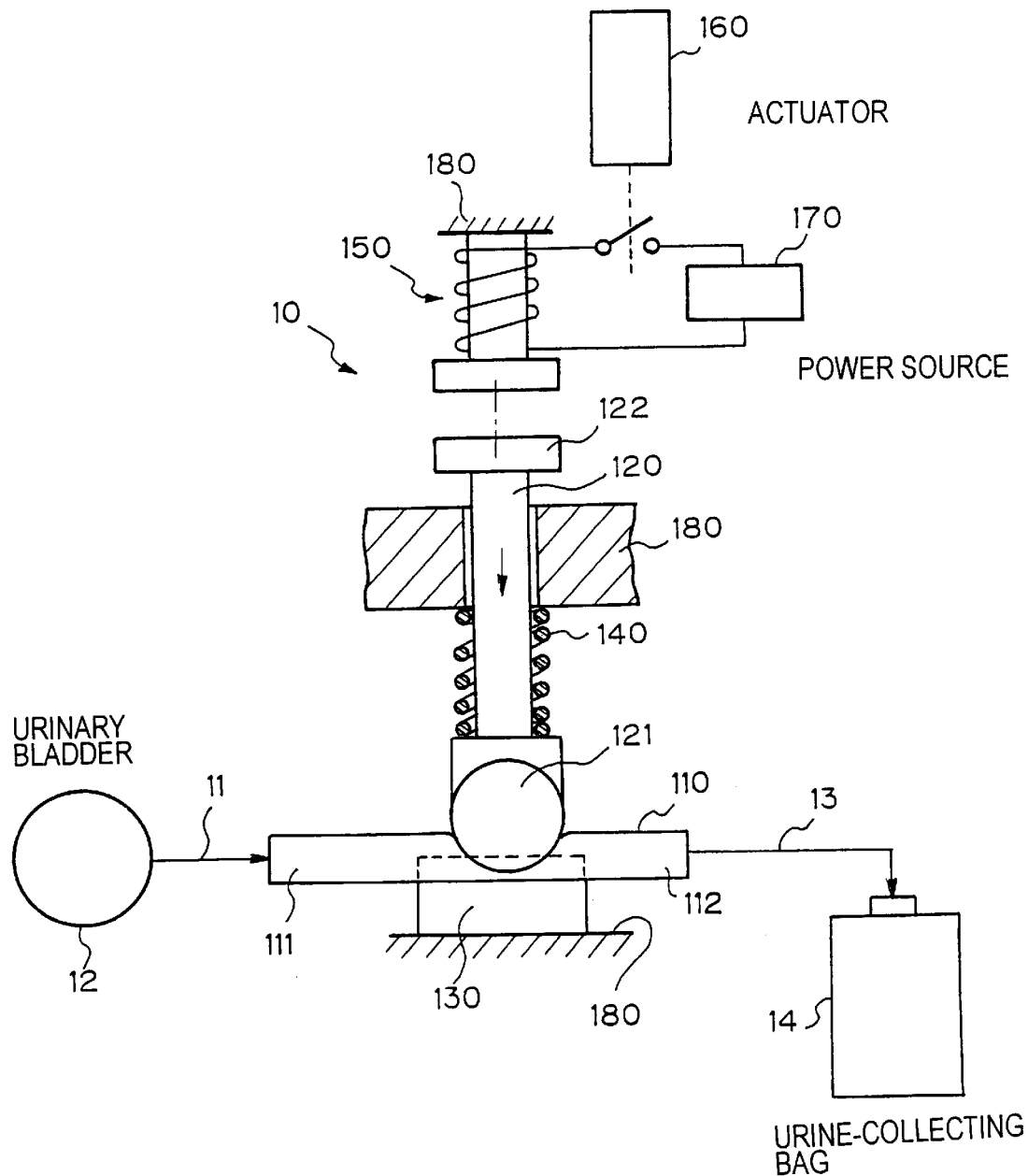
FIG. 2 is a schematic longitudinal sectional view of the urination apparatus of the present invention, illustrating a principle of the apparatus.
Figure 3:
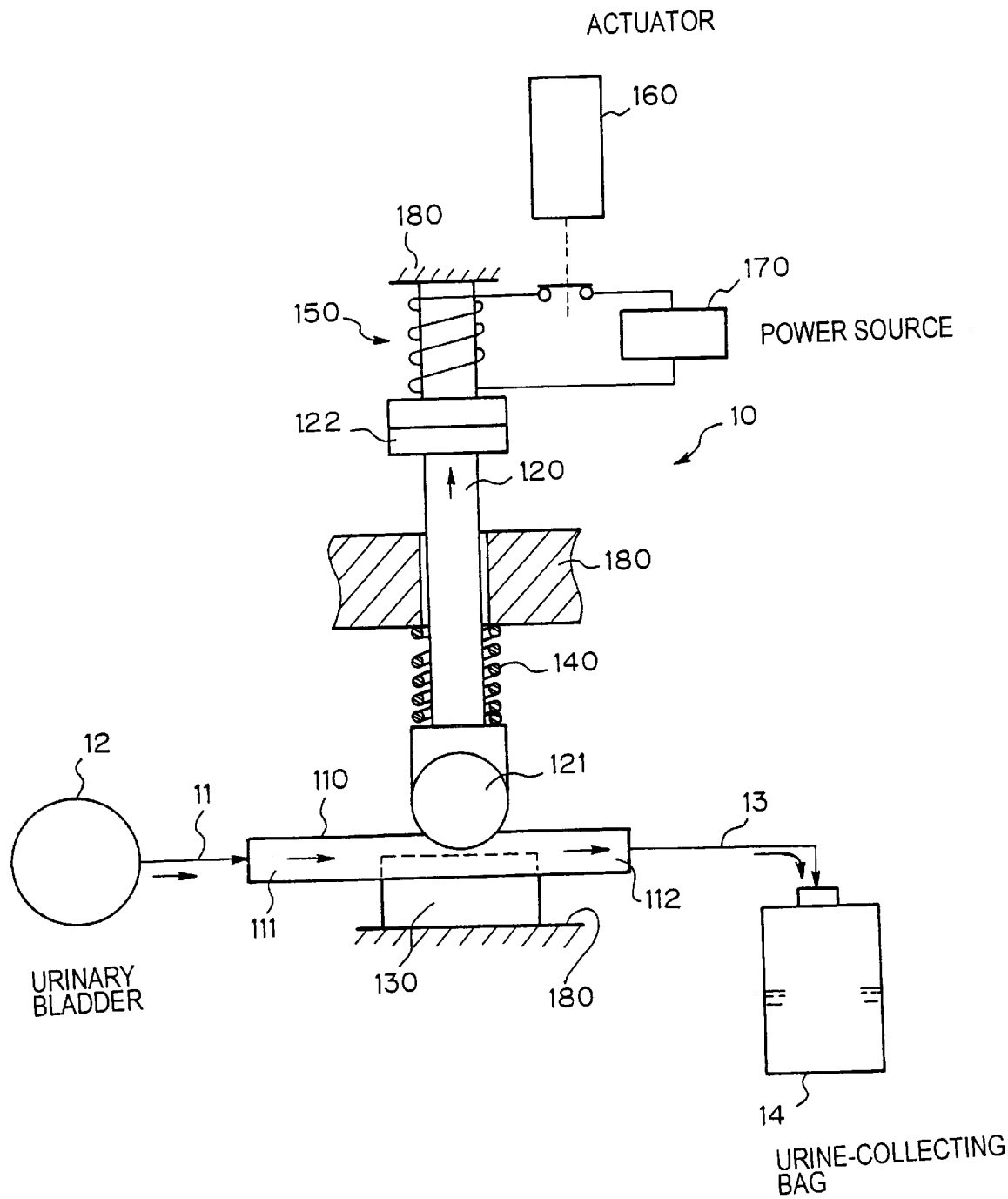
FIG. 3 is a similar view to FIG. 2, illustrating a state of urination operation.

As shown in FIGS. 1 through 3, a simple automatic opening and closing type of urination apparatus 10 in accordance with the present invention mainly comprises a flexible tube 110, a plunger 120, a bearing table 130, an elastic member 140, an electromagnetic solenoid 150, and an actuator 160.

The flexible tube 110 has an inlet port 111 and an outlet port 112. The plunger 120 has a pushing portion 121 at one end and a contact portion 122 at the other end. The bearing table 130 is disposed below the pushing portion 121 of the plunger 120 for supporting the flexible tube 110. The elastic member 140 normally biases the pushing portion 121 of the plunger 120 onto the flexible tube 110 on the bearing table 130 to squeeze the flexible tube 110 between the pushing portion 121 and the bearing table 130. The electromagnetic solenoid 150 selectively attracts and repulses the contact portion 122 of the plunger 120. The actuator 160 selectively couples the electromagnetic solenoid 150 to a power source 170.

In the above construction, the inlet port 111 of the flexible tube 110 is connected through a catheter 11 to a urinary bladder 12 and the outlet port 112 of the flexible tube 110 is connected through a conduit tube 13 to a urine-collecting bag 14. The electromangetic solenoid 150 is energized when a urine pressure in the urinary bladder 12 reaches a given value, thereby retracting the pushing portion 121 of the plunger 120 to release the flexible tube 110 from being squeezed (FIG. 3).

After completing urination, the actuator 160 deenergizes the electromagnetic solenoid 150, and the biasing force of the elastic member 140 advances again the pushing portion 121 of the plunger 120, thereby squeezing the flexible tube as described above (FIG. 2).

The actuator 160 may be any one of a balloon type pressure sensor, a timer, and a push button.

The power source 170 may be any one of an AC source, a dry battery, and a storage battery.

The bearing table 130, plunger 120, electromagnetic solenoid 150, and the like are contained in and supported on a conventional housing 180.

Figure 4:
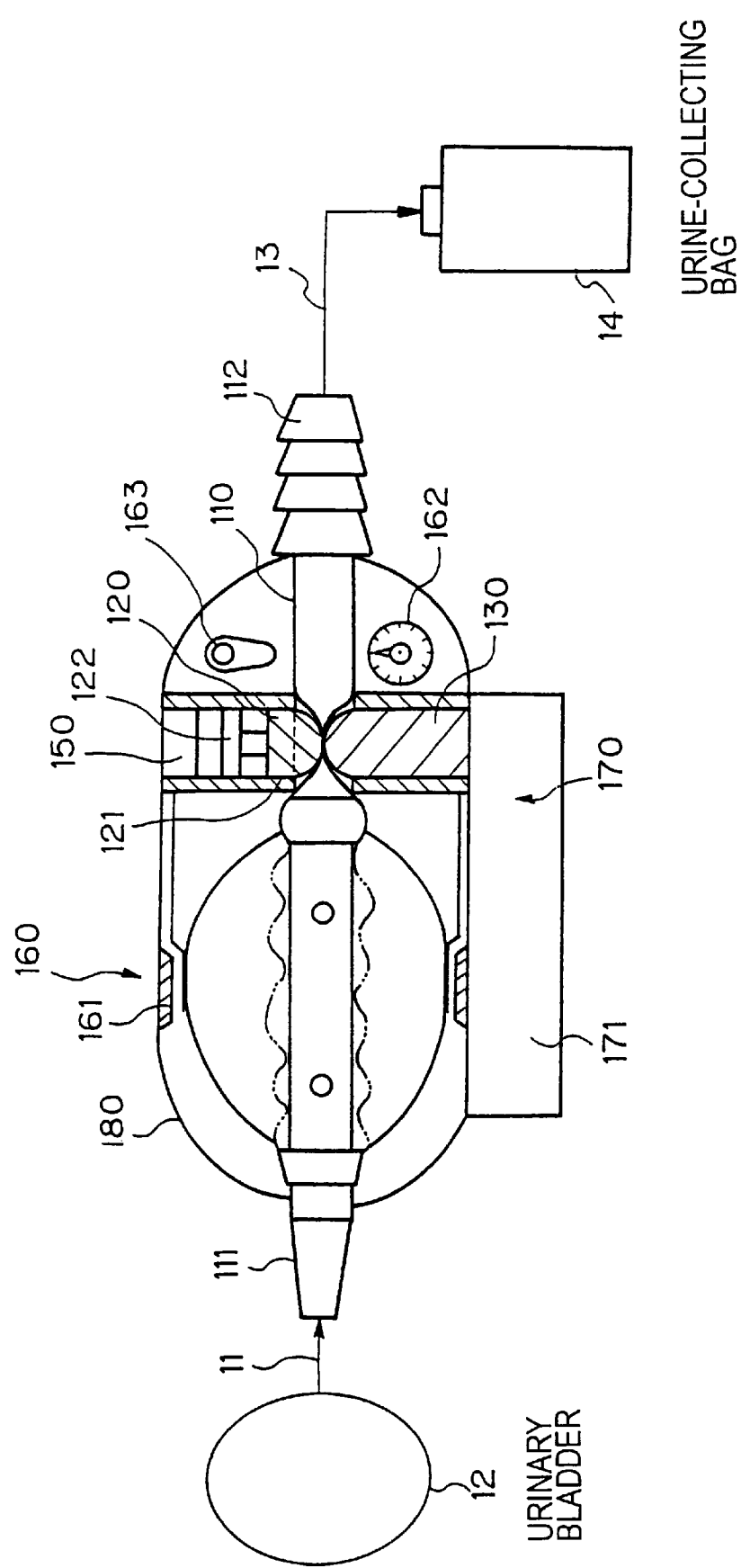
FIG. 4 is a schematic longitudinal sectional view of another embodiment of the urination apparatus in accordance with the present invention.

FIG. 4 shows another embodiment of a simple automatic opening and closing type of urination apparatus in accordance with the present invention. In this embodiment, the actuator 160 includes three kinds of actuators such as a balloon type pressure sensor 161, a. timer 162, and a push button 163. A dry battery 171 as a power source 170 is assembled together with a housing 180.

The balloon type pressure sensor 161 may include a structure in which a balloon is inflated by a urine pressure, thereby closing electrical contacts. The timer can set a urination timing in accordance with a personal physical condition. The push button 163 may be used when a user requires to urinate urgently.

Usually, a volume in a human urinary bladder is about 300 to 400 ml at a maximum and a urination pressure is about 50 to 400 mmHg at a maximum. However, since the volume and pressure are different due to personal sex, age, disease, and the like, it is preferable to set the urination pressure at about three steps (for example, 50 mmHg, 120 mmHg, and 200 mmHg) and to operate the actuator 160 in accordance with a personal situation.

Industrial Applicability

The present invention can be applied to a case of injecting a liquid medicine into a human body although the present invention is utilized as a urination apparatus. Further, the present invention can be applied to a common fluid appliance as well as a medical appliance.

What is claimed is:

1. A simple automatic opening and closing type of urination apparatus, comprising:

a flexible tube having an inlet port and an outlet port;

a plunger having a pushing portion at one end and a contact portion at the other end;

a bearing table disposed below said pushing portion of said plunger for supporting said flexible tube;

an elastic member for normally biasing said pushing portion of said plunger onto said flexible tube on said bearing table to squeeze said flexible tube between said pushing portion and said bearing table;

an electromagnetic solenoid for selectively attracting and repulsing said contact portion of said plunger; and an actuator for selectively coupling said electromagnetic solenoid to a power source;

wherein said inlet port of said flexible tube is connected through a catheter for connection to a urinary bladder and said outlet port of said flexible tube is connected through a conduit tube to a urine-collecting bag;

wherein said electromagnetic solenoid is energized when a urine pressure in the urinary bladder reaches a given value, thereby retracting said pushing portion of said plunger to release said flexible tube from being squeezed.

2. A simple automatic opening and closing type of urination apparatus according to claim 1, wherein said actuator is a balloon type pressure sensor.

3. A simple automatic opening and closing type of urination apparatus according to claim 1, wherein said actuator is a timer.

4. A simple automatic opening and closing type of urination apparatus according to claim 1, wherein said actuator is a push button.

5. A simple automatic opening and closing type of urination apparatus according to claim 1, wherein said power source is an AC source.

6. A simple automatic opening and closing type of urination apparatus according to claim 1, wherein said power source is a dry battery.

7. A simple automatic opening and closing type of urination apparatus according to claim 1, wherein said power source is a storage battery.

* * * * *

UNITED STATES PATENT AND TRADEMARK OFFICE
CERTIFICATE OF CORRECTION

PATENT NO. : 6,090,087
DATED : July 18, 2000
INVENTOR(S) : Osamu Tsukada, et al.

It is certified that error appears in the above-identified patent and that said Letters Patent is hereby corrected as shown below:

Change the Title of the Invention to read:

-- SIMPLE AUTOMATIC OPENING AND CLOSING TYPE OF URINATION APPARATUS --

Signed and Sealed this

Seventeenth Day of April, 2001

*Attest:*

NICHOLAS P. GODICI

*Attesting Officer*     *Acting Director of the United States Patent and Trademark Office*